United States Patent [19]

Vicario

[11] Patent Number: 4,767,600
[45] Date of Patent: Aug. 30, 1988

[54] EQUIPMENT FOR RAPID, AUTOMATIC CHEMICAL-CLINICAL ANALYSIS

[75] Inventor: Guido Vicario, Milan, Italy

[73] Assignee: Finbiomedica S.r.l., Milan, Italy

[21] Appl. No.: 746,583

[22] Filed: Jun. 19, 1985

[30] Foreign Application Priority Data

Jun. 19, 1984 [IT] Italy ............................... 21496 A/84

[51] Int. Cl.⁴ .......................................... G01N 35/02
[52] U.S. Cl. ........................................ 422/65; 422/63;
  422/73; 422/100; 422/102; 435/293; 435/301;
  436/807; 436/809; 901/36
[58] Field of Search ..................... 422/63-67,
  422/72, 73, 101, 102, 104; 435/293, 300, 301;
  901/36

[56] References Cited

U.S. PATENT DOCUMENTS

| | | |
|---|---|---|
| 3,344,702 | 10/1967 | Wood et al. |
| 3,504,259 | 3/1970 | Dalton. |
| 3,578,412 | 5/1971 | Martin .................... 422/65 |
| 3,731,820 | 5/1973 | Niki et al. ............... 901/26 |
| 3,847,486 | 11/1974 | McCabe. |
| 3,885,678 | 5/1975 | Borg et al. .............. 901/26 |
| 3,897,216 | 7/1975 | Jones ...................... 422/65 |
| 3,985,507 | 10/1976 | Litz ........................ 23/253 R |
| 4,011,048 | 3/1977 | Johnson, Jr. et al. .... 422/63 |
| 4,053,284 | 10/1977 | Posch. |
| 4,055,752 | 10/1977 | Kappe et al. |
| 4,141,954 | 2/1979 | Shigetomi ............... 422/64 |
| 4,259,290 | 3/1981 | Suovaniemi et al. .... 422/65 |
| 4,330,627 | 5/1982 | Thomas et al. .......... 435/301 |
| 4,351,799 | 9/1982 | Gross et al. ............. 422/100 |
| 4,387,991 | 6/1983 | Gilford et al. |
| 4,452,759 | 6/1984 | Takekawa ............... 422/73 |
| 4,457,896 | 7/1984 | Clark et al. ............. 422/73 |
| 4,463,097 | 7/1984 | Gurgan ................... 422/72 |
| 4,478,094 | 10/1984 | Salomaa et al. ........ 422/100 |
| 4,495,149 | 1/1985 | Iwata et al. ............. 422/65 |
| 4,681,742 | 7/1987 | Johnson .................. 422/65 |

FOREIGN PATENT DOCUMENTS

| | | | |
|---|---|---|---|
| 72284 | 2/1983 | European Pat. Off. |
| 55-71951 | 5/1980 | Japan .................... 422/65 |
| 56-2561 | 1/1981 | Japan .................... 422/73 |
| 58-48858 | 3/1983 | Japan .................... 422/63 |
| 58-62542 | 4/1983 | Japan .................... 422/73 |
| 58-82164 | 5/1983 | Japan .................... 422/63 |
| 58-105065 | 6/1983 | Japan .................... 422/63 |

Primary Examiner—Michael S. Marcus
Attorney, Agent, or Firm—Young & Thompson

[57] ABSTRACT

A detecting device is fitted so as to span a row of adjoining receptacles which are set in a reciprocating continuous motion, so that each receptacle passes within the scanning field of the detecting device. The latter sends the signals sequentially to a processor for elaboration into point curves showing the courses of each reaction through time. The row of receptacles may be set in a reciprocating motion by a rack, a stepping motor, a cam-type control or a coupling device, etc.

4 Claims, 5 Drawing Sheets

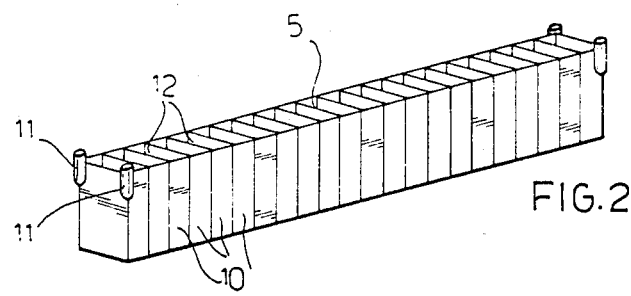
FIG. 2
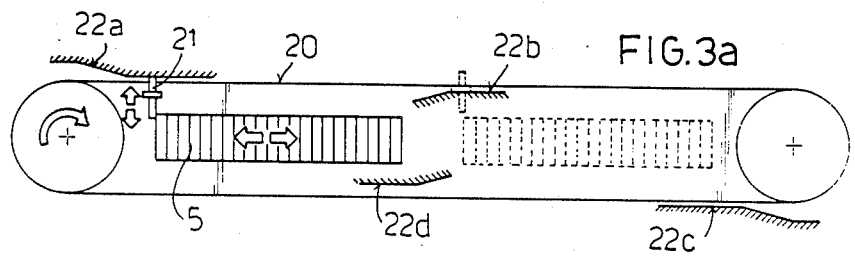
FIG. 3a
FIG. 3b
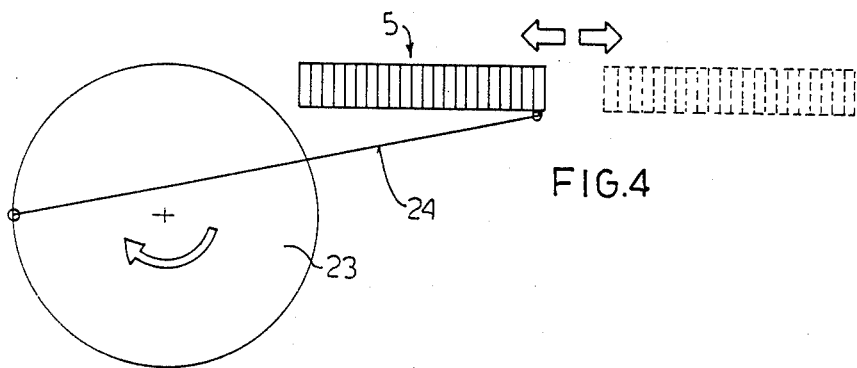
FIG. 4
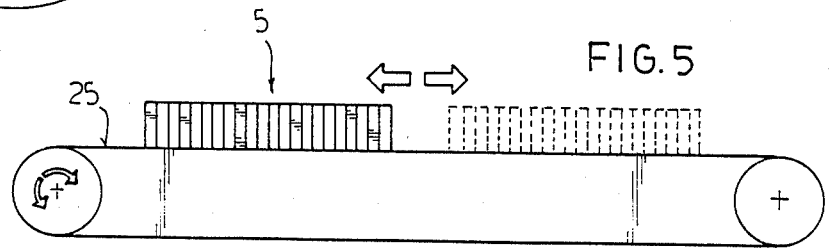
FIG. 5

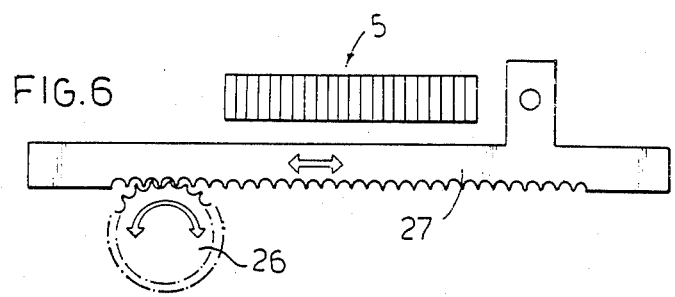
FIG.6
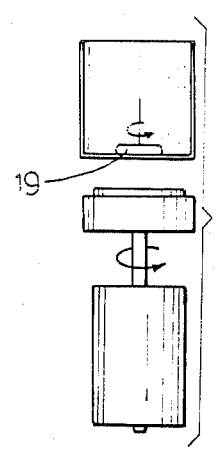
FIG.7
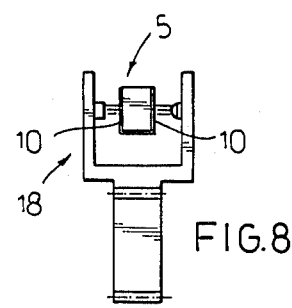
FIG.8
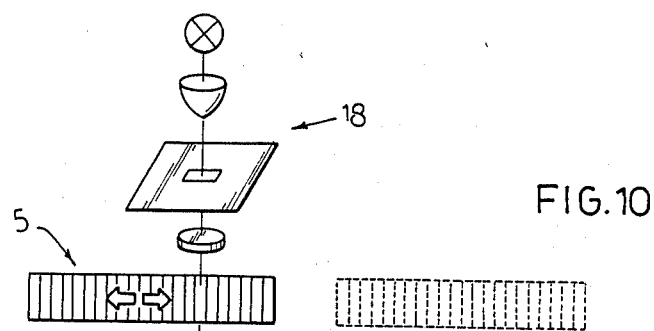
FIG.10
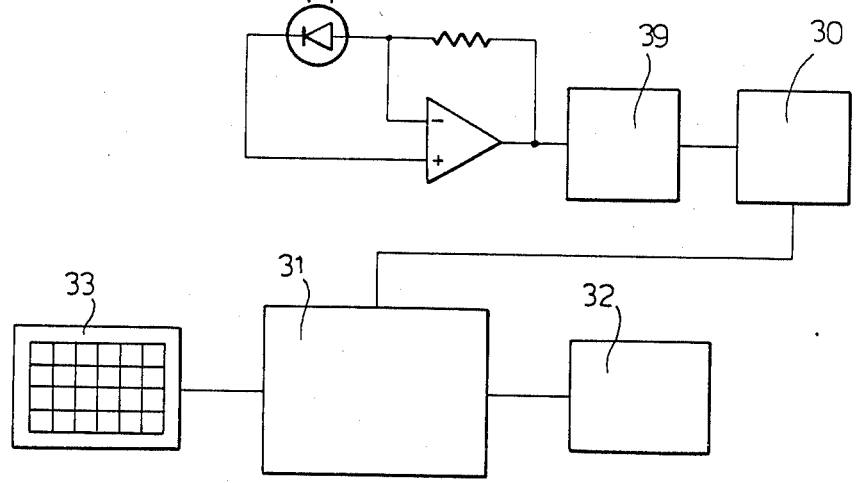

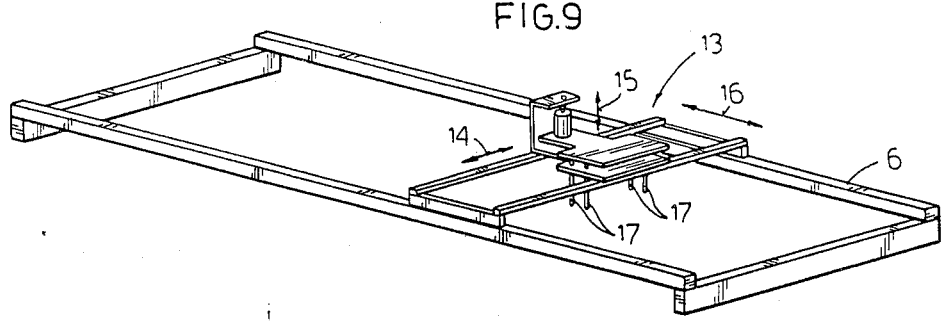
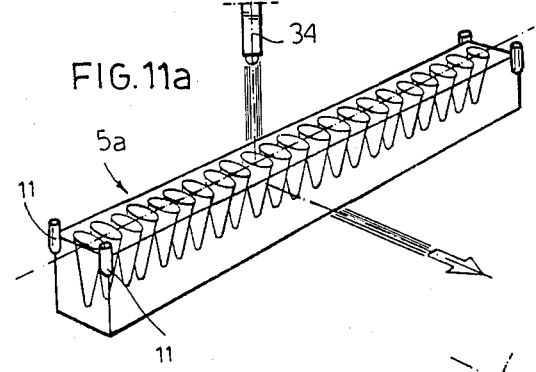
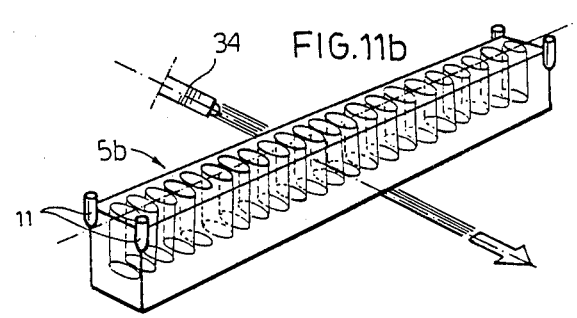
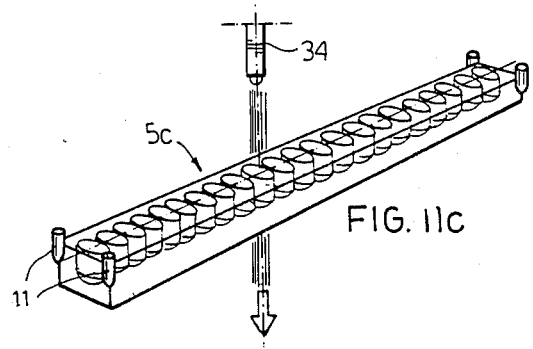

EQUIPMENT FOR RAPID, AUTOMATIC CHEMICAL-CLINICAL ANALYSIS

The present invention concerns the method and equipment for automating clinical analysis, especially in cases where a series of consecutive values must be obtained. All methods tried so far have revealed defects, limits, inconveniences, been too slow and required manual intervention. As a result, many methods already discovered have been inevitably shelved and the search for new ones stimulated. In particular, the following have been used:

(1) Discrete, large-volume systems with formed motion on a twelve position (analyses) conveyor belt. These systems have been shelved due to the high consumption of reagents and their limited flexibility (only 12 analyses).

(2) The system with one main conveyor belt (for the samples) and any desired number of secondary belts (for the reactions) with end readers for values and EDP coordination. This system is slow, bulky and very expensive.

(3) The multichannel, continuous-flow system. This causes big problems of subsequent samples being contaminated in the reaction tubes, leading to very imprecise results. Moreover, it is unable to select only the required reactions and is slow and very inflexible. To change one analysis program for another is a very complex operation.

(4) The centrifugal system. It is very fast, but needs a lot of manual intervention to change plates for each analysis. Furthermore, considerable manual intervention is also required, with the possibility of error, for matching the separator positions with the samples arranged on the series of plates.

(5) Multiple systems using optical fibers. A simultaneous, static reading occurs with the number of photodetectors corresponding to the number of channels used. An identical readout is not achieved, because of the photodetectors being different. The stage for preparing the reagents has not been automated. Computer elaboration is good but a lot of manual intervention is required in the intermediate stages. It cannot be considered an automatic, but rather a semiautomatic system.

(6) Sequential systems with reading of samples on a conveyor belt, but with random arrangement of both samples and reactions. This type of system is slow. The samples are read one by one and for the kinetic reactions it is necessary to wait for the reaction to develop or to reduce the reading time, resulting in a decrease in accuracy.

U.S. Pat. No. 3,344,702 is also known. This patent shows a set of adjoining receptacles which are not dealt with as a unit. No provision is made for automatically handling the receptacles. They must be moved by hand one at a time.

The aim of the invention in question is to eliminate all these defects and provide a very versatile and quick-operating piece of equipment. In fact, it is able to:

(1) accept all samples in a random order and analyse them in batches of 20, 50 or 100 at a time (or more);
(2) accept just one sample for urgent cases;
(3) simultaneously produce all the reactions required for each sample, likewise in batches of 20, 50, 100 or more at a time;
(4) add reagents only for the reactions required and not for all reactions (selective);
(5) simultaneously agitate and therostat all samples, allowing them to be incubated for as long as required;
(6) simultaneously read very rapidly the end point reactions with final, stable colouring of batches of 20, 50, 100 samples and repeatedly at very close intervals the kinetic reactions. In practice, the time needed is reduced in proportion to the number of sections used (20, 50, 100 or more). The same method of fluorescent and nephelometric reading is used;
(7) elaborate without manual intervention all the EDP data, store and coordinate the analytical reports by sample and analysis and supply all the statistical data required: day, month, year frequency; progressive figures; statistics for each type of analysis; pathological percentages and calculation of standard error;
(8) allow automatic check of errors (deviation) by the use of standard deviations intercalculated with the samples, the readings being automatically corrected by shifting the zero line and the optimal reading values, etc.;
(9) allow multiple applications with different types of reaction such as, study of coagulation, reading of blood groups, yet or no type reactions, immunoturbidimetric reactions, immunoenzymatic reactions, etc.;
(10) carry out any chemical process, even the most complex and arduous, add an unlimited number of reagents, add solid reagents or solid carriers, for example globular types composed of reagents or enzymes or immunoenzymatic material; and then remove the reagents after the reaction, wash the solid carriers, incubate the samples or reactions in course, thermostat, etc.

The main aim has been achieved by fitting a detecting device which spans a row of adjoining receptacles. These are set in a reciprocating motion, so that each receptacle passes within the scanning field of the optical detecting device, which sends the signals in a sequence to a processor for elaboration into point curves showing the course of the reaction through time.

The row of receptacles may be set in motion by a rack, a stepping motor, a cam-type control or a coupling device, etc.

A bridge crane is also fitted for moving the row of receptacles which usually have magnets attached. There are also rows of microsyringes for withdrawing and introducing reagents into each receptacle.

In addition, it is possible to introduce globules whose surfaces are covered with reagent molecules. In this case the receptacle is shaped so that the globule drops into one section only, whereas the other section contains the feed and withdrawal tubes for the reagent or washing solution. The two sections are connected by a narrow passage through which the globule is unable to pass.

This invention will now be explained in greater detail with the aid of the actual examples depicted in the enclosed drawings, in which:

FIG. 2 is a perspective view of a row of receptacles;

Figure 12A:
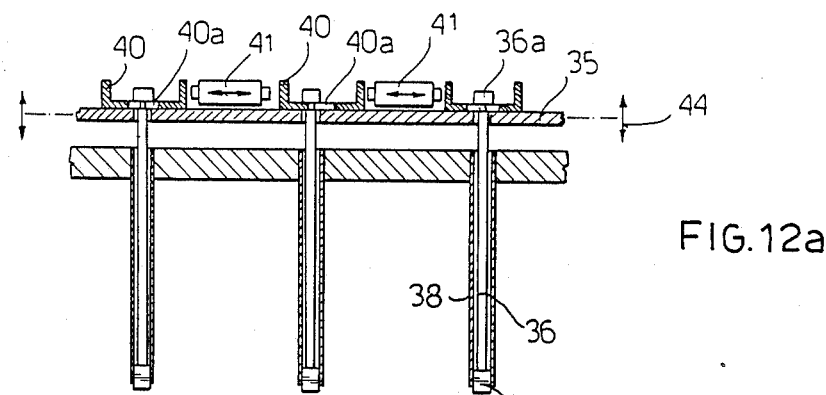
Figure 12B:
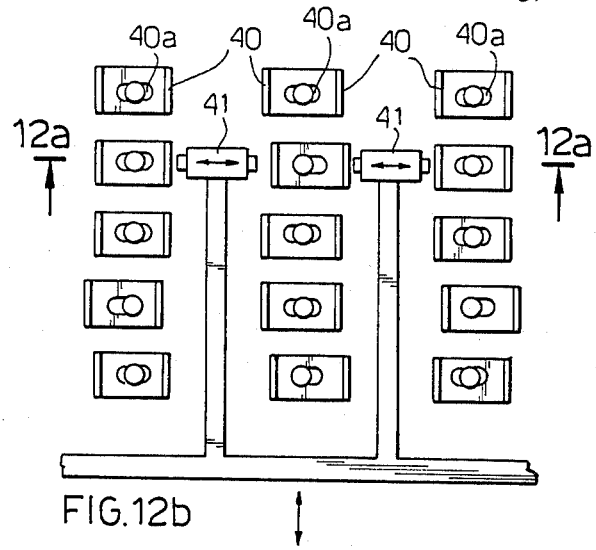
Figure 13B:
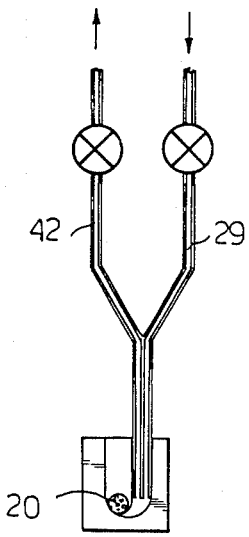
Figure 13A:
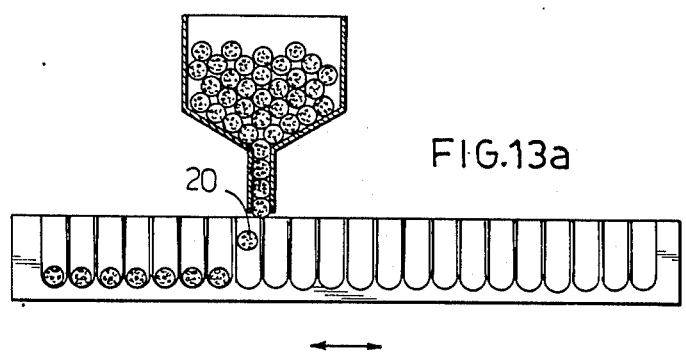
Figure 13C:
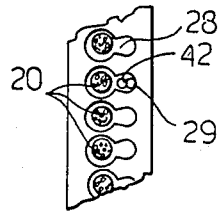

FIGS. 3 a and 3b are a side view and a top view respectively of a first device for giving the reciprocating motion;

FIG. 4 is a side view of a second device as an alternative to the one shown in FIGS. 3a and 3b;

FIG. 5 is a schematic view of a third device as an alternative to the one shown in FIGS. 3a and 3b;

FIG. 6 is a schematic view of a fourth device as an alternative to the one shown in FIGS. 3a and 3b;

FIG. 7 is a side view of a receptacle and an agitator;

FIG. 8 is a view of an optical-type detecting device;

FIG. 9 is a view of the bridge crane;

FIG. 10 shows the flow chart for the detecting device;

Figs. 11a to 11c are perspective views of different kinds of receptacles;

FIGS. 12 a and 12b are views of a vertical section along the line 11—11 of FIG. 11b and a plan of a system of microsyringes respectively;

FIGS. 13a, 13b and 13c are views which show a row of special receptacles into which reactive globules can be introduced.

Figure 1:
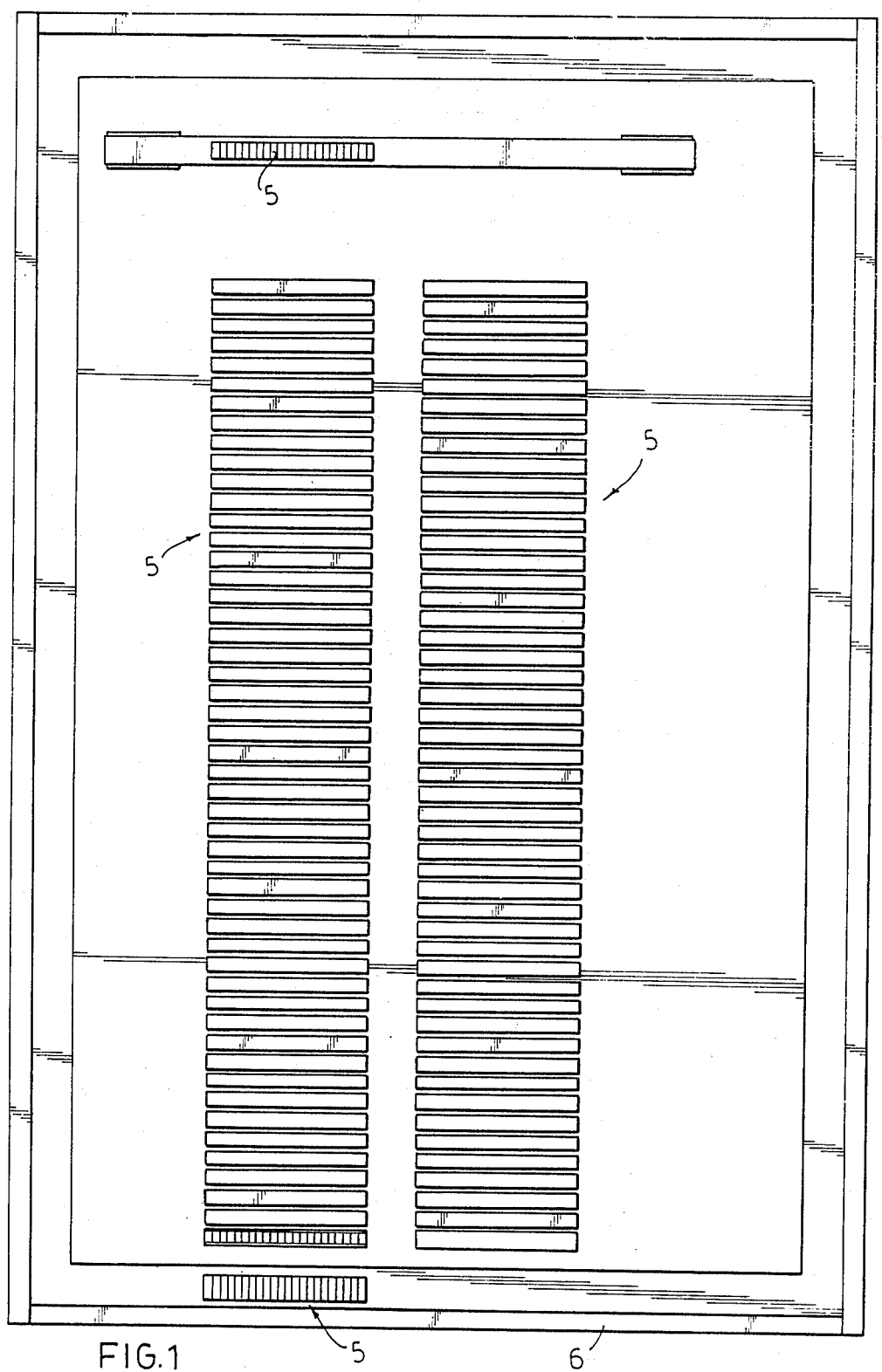
FIG. 1 is a top view of the equipment in question with two rows of receptacles side by side, ready to be moved towards the detecting device with a reciprocating motion.

The equipment in question 10 (FIGS. 1 and 2) includes a support frame 6, inside of which are housed rows of adjoining receptacles 12 forming the set 5 of receptacles.

The invention in question has a device which gives a reciprocating motion to a set of receptacles 5 (FIG. 2), made up of a row of adjoining receptacles 12. There are different versions of the actuating device. In FIGS. 3a and 3b a conveyor belt 20 is fitted with a coupling device 21, moved by cams 22a, b, c and d which move the coupling device to and from the set of receptacles 5.

In another version (FIG. 4) there is a rotating disk 23 with a rod 24 pivoted on its edge. The outer end of the rod is pivoted on the set of receptacles 5. FIG. 5, on the other hand, shows an actuating device which uses a conveyor belt on which the set of receptacles 5 is fitted. The conveyor belt 25 is moved in both directions by a stepping motor, which is not depicted.

FIG. 6 shows another actuating device which uses a pinion 26 and rack 27, on which the set of receptacles 5 is fitted. The pinion is moved in both directions.

All of these devices are able to move the set of receptacles 5 in a cycle from right to left and viceversa. The actuating device giving a back-and-forth motion allows each receptacle forming the set to pass at each cycle in front of one or more detecting devices 18 (for example, of the optical-photoelectric type) and undergo photometric analysis at a high repetition rate.

This ensures the possibility of carrying out many series of readings of slow reaction analysis (kinetic reactions), whose incremental values stabilize through time. It also ensures that with the use of suitable detecting devices the following can be read: all end point, fluorimetric, immunoturbidimetric, coagulation and blood group reactions.

A set is moved by a handling device. This set has many sections formed the receptacles 12 and four coupling devices 11 (for example, magnets), fitted at the top of each corner. These are for moving the set of receptacles by means of the bridge crane 13 depicted in FIG. 9. Each receptacle has two transparent sides 10 (FIG. 8) which allow reading by the detecting device 18. Magnetic microbars 19 (FIG. 7) can be fitted to the set of receptacles. They are moved by a motor equipped with a magnetic device 43 in order to give a shaking action. Solid carriers 20, for example globular immunoenzymes (FIG. 13a), can be used with this set. The special version can be washed continuously with suitable reactive solutions (FIGS. 13b and 13c), even when containing the above-said solid carriers 20. In this case, each receptacle 12 has an 8-shaped section (seen in FIG. 13c), in which a narrowing prevents contact between the solid carrier 20 and the tubes 29 and 42 for introducing and withdrawing the reagents or solutions.

The set of receptacles seen in FIG. 2 can be used for fluorimetric analyses. For nephelometric analyses it is better to use the set of receptacles 5a depicted in FIG. 11a, through which a beam of light from a lamp 34 passes. Chemical-clinical analyses in which the optical density is measured are carried out using set of receptacles like 5b (FIG. 11b), whose single receptacles are cylindrical. Finally, there are the set of receptacles 5c (FIG. 11c) used for analyses in which the state of aggregation of blood groups is read.

A bridge crane 13 (FIG. 9) which can be moved in the three directions 14, 15 and 16 respectively may also be included in the equipment in question. It is fitted with four holding devices, for example automatic, magnetic grippers 17, for moving the set of receptacles 5. These holding devices are positioned in line with the coupling devices on the set of receptacles 5.

The detecting device 18 (FIG. 10), for example the optical-photoelectric type, is suitable for detecting the values from the set of receptacles at high speed and repeating the detecting at each cycle. It sends all the data collected to an A/D converter 39, an interface 30 and a CPU and printer 31, and then onto a floppy disk 32. In this way a printed readout 33 is provided for each sample analysed.

A multiple system of automatically selected microsyringes 34 (FIG. 12a) may also be included. It serves to introduce reagents or solutions at consecutive moments. It is fitted with a plate 35 which moves vertically (arrow 44) and is connected to a number of pistons 36 with plungers 37 made of a material suitable for use in a glass (or other material), capillary sleeve 38. The result is a multiple, capillary microsyringe. An electromagnetic device activates or deactivates a series of keys 40 with slits 40a which engage or disengage the head 36a of each piston 36. The keys are moved by pushing devices 41. FIG. 12a shows only one microsyringe being operated by the plate's 35 vertical movement.

Furthermore, the equipment can be fitted with a filtering device for separating and retrieving the filtrates from the top part of the solution, as well as a device for separating, retrieving and treating two or more products.

What we claims is:

1. Apparatus for carrying out chemical-clinical analyses of a plurality of chemical reactions, said apparatus comprising: a row of integral receptacles for receiving samples to be analyzed; an actuating device for continuously repetitively moving the receptacles back and forth along a horizontal path of oscillatory movement; a detector means, such that the samples in the receptacles can be sequentially, repeatedly and continually subjected to a field of the detector means by the actuating device; and processor means to process and store data received from the detector means wherein values for each of said plurality of reactions may be detected at predetermined intervals for a predetermined length of time and recorded in a memory device, for use with solid carriers, said apparatus further comprising a motor for shaking said receptacles, and means for continuously washing solid carriers contained in said receptacles with liquid washing solutions, said receptacles being designed in a U-shape with a curved bottom and having an 8-shape cross section over a substantial height such that said receptacles contain two circular portions, said portions being side by side, and which communicate to enclose a single total volume.

2. Apparatus according to claim 1 in which one said portion of said 8-shaped receptacle is of larger diameter than the other said portion such that a solid carrier may be contained in said larger diameter portion and not pass to said other portion, said apparatus further comprising a feed tube and a withdrawal tube for introducing a liquid into said other portion of said 8-shaped receptacle so that said liquid may pass into said larger diameter portion of said receptacle to contact said solid carrier before being removed.

3. Apparatus for carrying out chemical-clinical analyses of a plurality of chemical reactions, said apparatus comprising: a row of integral receptacles for receiving samples to be analyzed, for use with solid carriers, and means for continuously washing solid carriers contained in said receptacles with liquid washing solutions, said receptacles being designed in a U-shape with a curved bottom and having an 8-shape cross section over a substantial height such that said receptacles contain two portions of circular cross section, said portions being side by side, and which communicate to enclose a single total volume, one said portion receiving a solid carrier, said washing means being disposed in the other said portion.

4. Apparatus according to claim 3, in which said one portion of said 8-shaped receptacle is of larger diameter than said other portion such that a solid carrier may be contained in said larger diameter portion and not pass to said other portion, said washing means comprising a feed tube and a withdrawal tube for introducing a liquid into said other portion of said 8-shaped receptacle so that said liquid may pass into said larger diameter portion of said receptacle to contact a solid carrier before being removed.

* * * * *

UNITED STATES PATENT AND TRADEMARK OFFICE
CERTIFICATE OF CORRECTION

PATENT NO. : 4,767,600
DATED : August 30, 1988
INVENTOR(S) : Guido VICARIO et al.

It is certified that error appears in the above—identified patent and that said Letters Patent is hereby corrected as shown below:

Title page:

In the surname of the inventor, in Item 19, change "Vicario" to --Vicario et al.--.

In Item 75, change "Inventor: Guido Vicario, Milan, Italy" to --Inventors: Guido Vicario and Cesare Vicario, both of Milan, Italy--.

Signed and Sealed this

Second Day of April, 1991

Attest:

HARRY F. MANBECK, JR.

Attesting Officer

Commissioner of Patents and Trademarks